United States Patent [19] [11] 4,042,693
Delarge et al. [45] Aug. 16, 1977

[54] DERIVATIVES OF 1,2,4-THIADIAZINE

[75] Inventors: Jacques E. Delarge, Dolembreux; Charles L. Lapière, Tongeren; André H. Georges, Ottignies, all of Belgium

[73] Assignee: A. Christiaens Societe Anonyme, Brussels, Belgium

[21] Appl. No.: 694,422

[22] Filed: June 9, 1976

Related U.S. Application Data

[63] Continuation-in-part of Ser. No. 568,759, April 16, 1975.

[30] Foreign Application Priority Data

Apr. 14, 1975 United Kingdom ............... 16836/75

[51] Int. Cl.$^2$ .................... C07D 285/24; A61K 31/54
[52] U.S. Cl. ........................................ 424/246; 544/10
[58] Field of Search ................................... 260/243 R

[56] References Cited

U.S. PATENT DOCUMENTS 3,819,639  6/1974  Delarge et al. .................. 260/243 R Primary Examiner—John M. Ford
Attorney, Agent, or Firm—Sughrue, Rothwell, Mion, Zinn and Macpeak

[57] ABSTRACT

This invention relates to new derivatives of 1,2,4-thiadiazine having anti-inflammatory properties.

The new derivatives of 1,2,4-thiadiazine may be represented by the following general formula:

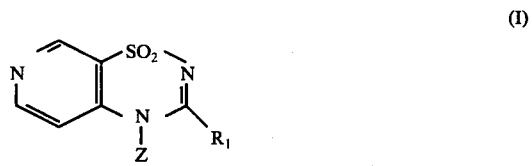

in which $R_1$ and Z each represent an unsubstituted or substituted phenyl group.

This invention relates also to the N-oxides of the compounds of formula I, as well as to the acid and base addition salts of said compounds.

6 Claims, No Drawings

DERIVATIVES OF 1,2,4-THIADIAZINE

This application is a continuation-in-part of application Ser. No. 568,759, filed Apr. 16, 1975.

BRIEF DESCRIPTION OF THE INVENTION

This invention relates to new derivatives of 1,2,4-thiadiazine, their preparation and use.

The new derivatives of 1,2,4-thiadiazine are of the following general formula:

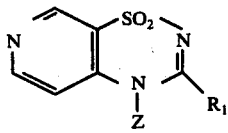

(I)

in which $R_1$ represents an unsubstituted phenyl group or a phenyl group substituted by a halogen atom, and Z represents an unsubstituted phenyl group or a phenyl group substituted by one or two halogen atoms or by a $C_1-C_4$ alkyl or alkoxy group or by the triflurormethyl group.

The invention also relates to the N-oxides of the compounds of formula I in which the oxygen atom is attached to the nitrogen atom of the pyridin moiety, and to the base and acid addition salts of said compounds of formula I.

DETAILED DESCRIPTION OF THE INVENTION

The compounds according to this invention, i.e. the compounds of formula I, may be prepared by the following processes.

First Process

A 3-benzoylsulfonamido-4-phenylamino pyridine of the formula:

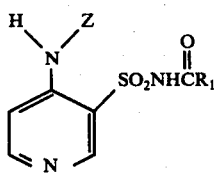

(II)

in which Z and $R_1$ have the meanings given above, being a compound according to copending application Ser. No. 568,759 is treated with a dehydrating agent such as acetic acid anhydride, whereby it cyclizes to a compound of formula I.

Second Process

A 3-sulfonamido-4-phenylamino pyridine of the formula:

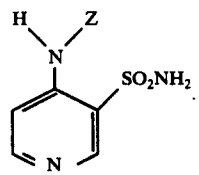

(III)

in which Z has the meanings given above, is reacted with an anhydride of an aryl carboxylic acid of the formula:

$(R_1CO)_2O$ (IV)

or with a chloride of an aryl carboxylic acid of the formula:

$R_1COCl$ (V)

in which $R_1$ has the meanings given above, whereby one obtains on the one hand a first yield of the corresponding compound of formula I, and on the other hand a yield of corresponding compound of formula II, which may be treated according to the first process described hereabove, in order to give a second yield of the compound of formula I.

When it is desired to obtain the N-oxides of the compounds of formula I, the above processes are applied, except that the corresponding N-oxides of the starting pyridine derivatives are used, or a compound of formula I is treated with meta-chloroperoxy-benzoic acid.

It has been found that the compounds of formula I have anti-inflammatory properties.

These properties have been determined by the following test.

PHARMACOLOGICAL TEST FOR ANTI-INFLAMMATORY PROPERTIES

The compounds to be tested are given as freshly prepared solutions or suspensions by oral route one hour before injecting the paw of rats with carrageenan which is a known inflammatory agent.

The inflammatory agent (carrageenan) either in solution or suspension is then injected into the plantar tissue of the right hind paw of each rat, the left paw remaining untreated and serving as control. Each animal receives, for example, 0.05 ml of an aqueous solution containing 1% by weight of carrageenan and 0.9% of sodium chloride.

4 Hours after the injection of the inflammatory agent, the importance of swelling is determined by plethysmography and is expressed as a percent of the volume of the control paw.

The anti-inflammatory effect expressed as a percentage of inhibition is obtained by comparison between rats treated with the anti-inflammatory compound and a control group of rats.

The results of the tests made with compounds which are representative of this invention are given in the following table:

TABLE

| Compound of Example | Z | $R_1$ | % inhibition of acute oedema |
|---|---|---|---|
| 1 | 3-trifluoro-methylphenyl | phenyl | 53.6 |
| 2 | 3,5-dichlorophenyl | parachlorophenyl | 57 |
| 3 | 3-ethylphenyl | " | 60 |
| 4 | 3-methoxyphenyl | orthochlorophenyl | 40 |

This invention relates therefore also to pharmaceutical compositions containing as active ingredient at least one compound of the formula I or a N-oxide of such a compound or a base- or acid-addition salt thereof, together with a pharmaceutically acceptable vehicle or carrier.

The compounds of this invention may be administered in the form of dragees, tablets, capsules and suppositories at daily doses of 50 to 300 mg of active compound.

EXAMPLES

The following examples illustrate the preparation of compounds of formula I.

EXAMPLE 1

Preparation of
3-phenyl-4-metatrifluoromethylphenyl-4H-pyridino-[4,3-e]-1,2,4-thiadiazine-1,1-dioxide (formula I : Z = metatrifluoromethylphenyl; $R_1$ = phenyl)

A. 3-benzoylsulfonamido-4-(3'-trifluoromethylphenyl)-aminopyridine is first prepared by heating a mixture of 0.01 mole of 4-chloro-3-benzoylsulfonamidopyridine, 0.01 mole of metatrifluoroaniline and a little amount of copper powder to about 80°C. A spontaneous heating occurs. The mixture is maintained during 10 minutes at about 80°–100° C and is then taken up with water and the pH is adjusted to 5. The obtained precipitate, consisting of 3-benzoylsulfonamido-4-(3'-trifluoromethylphenyl)-aminopyridine (m.p. : 249°C) is treated with acetic anhydride, whereby it cyclizes to form the title compound (m.p. 290° C).

B. 0.01 mole of 3-sulfonamido-4-(3-trifluoromethyl)-phenylaminopyridine, 0.030 mole of benzoyl chloride and 20 ml of anhydrous pyridine are left in contact with one another for 24 hours. The resulting mixture is poured into NaOH (10%). One obtains a precipitate of the cyclized title product (m.p. 290° C) and a solution. When neutralized by acetic acid, the solution gives a precipitate of impure 3-benzoylsulfonamido-4-(3'-trifluoromethylphenyl)-amino-pyridine. By treatment with a dehydrating agent, such as acetic anhydride, this compound is converted into the title compound.

EXAMPLE 2

Preparation of
3-parachlorophenyl-4-(3',5'-dichlorophenyl)-4H-pyridino-[4,3-e]-1,2,4-thiadiazine-1,1-dioxide (formula I : Z = 3,5-dichlorophenyl ; $R_1$ = 4-chlorophenyl)

Reacting 3-sulfonamido-4-(3', 5'-dichlorophenyl)-aminopyridine with parachlorobenzoyl chloride as described in Example 1B, one obtains a first yield of the title compound (yield 20%; m.p. 284°–286° C) and an amount of 3-parachlorobenzoylsulfonamido-4-(3',5'-dichlorophenyl)-aminopyridine (yield 50%; m.p. 300° C). This compound may be converted into the title compound by treatment with a dehydration agent, as described in Example 1.

EXAMPLE 3

Preparation of
3-parachlorophenyl-4-(3'-ethylphenyl)-4H-pyrido-[4,3-e]-1,2,4-thiadiazine-1,1-dioxide (formula I : Z = 3-ethylphenyl; $R_1$ = 4-chlorophenyl)

Reacting 3-sulfonamido-4-(3'-ethylphenyl)-aminopyridine with parachlorobenzoyl chloride as in example 1B, one obtains some 3-parachlorophenyl-4-(3'-ethylphenyl)-4H-pyrido-[4,3-e]-1,2,4-thiadiazine-1,1 dioxide (yield 5%; m.p. 227–229° C) and a greater amount of 3-parachlorobenzoylsulfonamido-4-(3'-ethylphenyl)-aminopyridine (yield 80%; m.p. 265–267° C), which is converted into the cyclized title compound by treatment with acetic anhydride as described in Example 1.

EXAMPLE 4

Preparation of
3-orthochlorophenyl-4-(3-methoxyphenyl)-4H-pyrido-[4,3-e]-1,2,4-thiadiazine-1,1-dioxide Reacting 3-sulfonamido-4-(3'-methoxyphenyl)-aminopyridine with orthochlorobenzoyl chloride as described in example 1A, one obtains mainly the title compound (yield 65%; m.p. 227°–229° C) and some 3-orthochlorobenzoyl-4-(3'-methoxyphenyl)-aminopyridine (yield 5%; m.p. 181°–183° C).

We claim:

1. A compound of the formula:

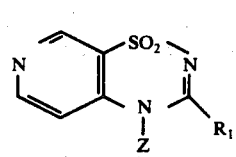

(I)

in which $R_1$ represents an unsubstituted phenyl group or a phenyl group substituted by a halogen atom, and Z represents an unsubstituted phenyl group or a phenyl group substituted by one or two halogen atoms or by a $C_1$–$C_4$ alkyl or alkoxy group or by the trifluoromethyl group, and the pharmaceutically acceptable base and acid addition salts of said compounds.

2. 3-phenyl-4-metafluoromethylphenyl-4H-pyridino-[4,3-e]-1,2,4-thiadiazine-1,1-dioxide.

3. 3-parachlorophenyl-4-(3',5'-dichlorophenyl)-4H-pyridino-[4,3-e]-1,2,4-thiadiazine-1,1-dioxide.

4. 3-parachlorophenyl-4-(3'-ethylphenyl)-4H-pyridino-[4,3-e]-1,2,4-thiadiazine-1,1-dioxide.

5. 3-orthochlorophenyl-4-(3'-methoxyphenyl)-4H-pyridino-[4,3-e]-1,2,4-thiadiazine-1,1-dioxide.

6. Pharmaceutical compositions containing at least one compound according to claim 1 as active ingredient in an anti-inflammatory effective amount, together with a pharmaceutical carrier or vehicle.

* * * * *